(12) United States Patent
Cai

(10) Patent No.: US 12,275,743 B2
(45) Date of Patent: Apr. 15, 2025

(54) METHOD FOR PREPARING NEAR-INFRARED REGION II FLUORESCENT SMALL MOLECULE

(71) Applicant: NANJING NUOYUAN MEDICAL INSTRUMENT CO.LTD, Nanjing (CN)

(72) Inventor: Huiming Cai, Nanjing (CN)

(73) Assignee: NANJING NUOYUAN MEDICAL INSTRUMENT CO.LTD, Nanjing (CN)

( * ) Notice: Subject to any disclaimer, the term of this patent is extended or adjusted under 35 U.S.C. 154(b) by 38 days.

(21) Appl. No.: 17/907,972

(22) PCT Filed: May 9, 2022

(86) PCT No.: PCT/CN2022/091633
§ 371 (c)(1),
(2) Date: Aug. 30, 2022

(87) PCT Pub. No.: WO2023/010925
PCT Pub. Date: Feb. 9, 2023

(65) Prior Publication Data
US 2024/0199633 A1 Jun. 20, 2024

(30) Foreign Application Priority Data
Aug. 3, 2021 (CN) .......................... 202110886270.7

(51) Int. Cl.
C07D 495/04 (2006.01)
C09K 11/06 (2006.01)

(52) U.S. Cl.
CPC ............ *C07D 495/04* (2013.01); *C09K 11/06* (2013.01); *C09K 2211/1018* (2013.01)

(58) Field of Classification Search
CPC .................................................... C07D 495/04
See application file for complete search history.

(56) References Cited

U.S. PATENT DOCUMENTS

| 2018/0259541 A1 | 9/2018 | Mandell et al. |
| 2020/0255667 A1 | 8/2020 | Sparr et al. |
| 2021/0015885 A1 | 1/2021 | Briesewitz et al. |

FOREIGN PATENT DOCUMENTS

CN 113461707 A * 10/2021

* cited by examiner

*Primary Examiner* — David K O'Dell
(74) *Attorney, Agent, or Firm* — Hemisphere Law, PLLC; Zhigang Ma

(57) ABSTRACT

The present disclosure provides a method for preparing a near-infrared region II fluorescent small molecule. The method utilizes organic full synthesis to construct a novel structured fluorescent probe small molecule, belonging to the fields of chemical sensing technology and fluorescence imaging. Compared with the currently studied fluorescent probe with a benzobisthiadiazole structure, the near-infrared region II fluorescent small molecule has the advantages of simple synthesis method, easy modification, stable structure, high fluorescence quantum yield and the like.

9 Claims, 4 Drawing Sheets

METHOD FOR PREPARING NEAR-INFRARED REGION II FLUORESCENT SMALL MOLECULE

TECHNICAL FIELD

The present disclosure provides a method for preparing a near-infrared region II fluorescent small molecule, and relates to the fields of chemical sensing technology and fluorescence imaging.

BACKGROUND

At present, a fluorescence microscopy imaging technology is one of the most widely used optical imaging techniques, and more and more attention has been paid to a near-infrared fluorescence living imaging technology that belongs to fluorescence imaging. The traditional fluorescence imaging mainly focuses on near-infrared region I (NIR-I) with a fluorescence a emitting wavelength range of 650-950 nm, a short wavelength (<1000 nm) and poor photon penetration depth which become major obstacles of living biomedicine fluorescence imaging applications. Compared with visible light and NIR-I light, the light capable of near-infrared region II (NIR-II) fluorescence imaging at a wavelength of 1000-1700 nm can penetrate through deeper biological tissues, and there are fewer scattered light at a window of this wavelength. Since NIR-II light has the advantages of deeper biological tissue penetration (about 5-20 mm), weakened background spontaneous fluorescence and improved signal-to-noise ratio, the emerging fluorescence imaging in NIR-II region has attracted more and more attention. Probes in NIR-II fluorescence imaging mainly include the following categories: rare earth elements, nano materials, carbon nanotubes, quantum dots, organic molecular polymers and organic small molecular compounds.

Generally, organic near-infrared region II fluorescent small molecules are mainly divided into three categories, in which the fast category is a near-infrared region II fluorescent small molecule with a benzobisthiadiazole structure as a main body. The probe is high in fluorescence quantum yield, but cumbersome in synthesis step and needs to use tin reagents with large toxicity for synthesis. The second category is a near-infrared region II fluorescent small molecule with a polymethyl as a main body, which is obtained by extending a near-infrared region I cyanine dye probe and replacing an electron donor group, but is poor in stability, easy to decompose under the irradiation of light and low in quantum yield. The third category is cyanine dye which has fluorescence tailing at 1000-1200 nm, is extremely low in fluorescence quantum yield, and has very high requirements for test instruments.

Accordingly, preparation of a near-infrared two region fluorescent small molecule with high fluorescence quantum yield, simple synthesis process, stable chemical structure, human safety and easy modification so as to further expand a near-infrared two region fluorescent small molecule library and make up for the shortcomings of other near-infrared region II fluorescent small molecules in practical use has high scientific research and clinical application values.

SUMMARY

The objective of the present disclosure is to provide a method for preparing a near-infrared region II fluorescent small molecule. Such the organic fluorescent molecule is simple to synthesize, stable in chemical structure, easy to modify and high in fluorescence quantum yield.

In order to achieve the above objective, the specific technical solution of the present disclosure is as follows:

Provided is a near-infrared region II fluorescent small molecule, wherein a near-infrared region II fluorescent small molecule with a D-π-A system structure is constructed by using a naphthalimide salt as a strong electron acceptor, dioxythiophene as a π bridge and an N, N-dimethylstyrene structure as an electron donor. Such the near-infrared region II fluorescent small molecule has the advantages of simple synthesis, stable chemical stability, easy modification, high fluorescence quantum yield and the like, and has huge development potential in the fields of tumor surgery navigation imaging and medical cell labeling. The structure of the naphthalimide salt F1 is as follows:

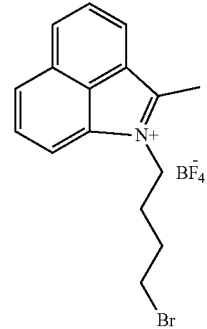

F1 the structure of the dioxythiophene F2 is as follows:

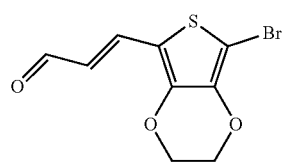

F2 the structure of the N, N-dimethylstyrene F3 is as follows:

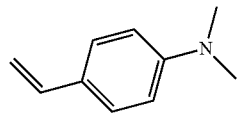

F3 the structure of the near-infrared region II fluorescent small molecule F4 is as follows:

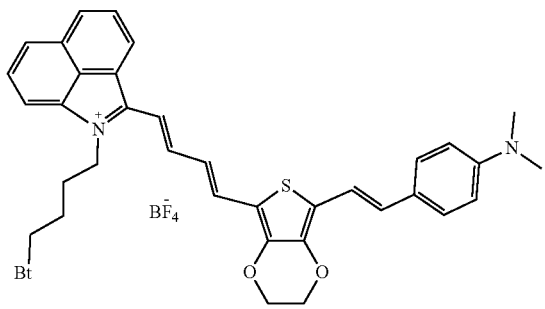

F4 the bromine group for electron donor is prone to further modifying a probe, and a dioxythiophene heterocycle is prone to stabilizing the structure of the small molecule.

Provided is a method for preparing a near-infrared region II fluorescent small molecule, comprising the following steps:

A, synthesis of intermediate I M1

Weighed N,N-dimethylformamide, Benz[cd]indol-2(1H)-one and anhydrous lithium hydroxide are successively added into a reactor with a stirrer and heated to 125-150° C. under the condition of stirring, air in the reaction system is replaced with nitrogen, weighed 1,4-dibromobutane is dropwise added under the protection of nitrogen, the reaction is preserved for 30-100 min, subsequently, a stabilizer is added, the above materials are stirred for 15-60 min and then subjected to reduced rectification, ethanol is added in a bottom liquid, and finally the intermediate I M1 is obtained by crystallizing, filtering and drying;

B, synthesis of naphthalimide salt F1 the intermediate I M1 is added into tetrahydrofuran and heated to 52-58° C. under the conditions of stirring and nitrogen protection, a methyl magnesium chloride solution is dropwise added, the above reaction is heated to 62-66° C. after dropwise addition is completed and then the reaction is preserved for 0.5-2.5 h, a solvent is recovered by distillation, a proper amount of water is added into a bottom liquid, a 20 wt % fluoroboric acid solution is slowly dropwise added at room temperature, a reaction speed is controlled, stirring is maintained for 0.5-1 h after dropwise addition is completed, and the naphthalimide salt F1 is obtained by suction filtration;

C, synthesis of dioxythiophene F2

5-bromo-2-(3,4-vinyldioxythiophene) formaldehyde and (formylmethylene) triphenylphosphine are mixed in a solution of toluene and heated to reflux, the reaction is maintained for 12-18 h, a solvent is evaporated at reduced pressure to obtain a crude product and the crude product is purified on a silica gel column, and white powdered dioxythiophene F2 is obtained by using a petroleum ether/dichloromethane mixture as an eluting agent;

D, synthesis of intermediate II M2 a metered catalyst 1 is added into N,N-dimethylformamide, 4-vinyl-N,N-dimethylaniline F3 and dioxythiophene F2 are successively added under the condition of stirring, then the mixed solution is heated to 125-150° C. and stirred to react for 12-20 h under the protection of nitrogen, the reaction solution is extracted with water and dichloromethane after the reaction is ended, each phase is separated, a combined organic phase is dried with $Na_2SO_4$, the solvent is evaporated at reduced pressure, and the left residue is purified by column chromatography to obtain the intermediate II M2; and E, synthesis of near-infrared region II small molecule F4 the intermediate II M2 and naphthalimide salt F1 are mixed in ethanol, a proper amount of catalyst 2 is added, the above materials are stirred for 4-12 h under the protection of nitrogen, a solvent is evaporated at reduced pressure after the reaction is ended, and then the left residue is purified by column chromatography to obtain the final product near-infrared region II small molecule F4 is obtained.

Preferably, in step A, heating is carried out under the condition of stirring to raise the temperature to 138-140° C.

Preferably, in step A, the stabilizer is a mixture of one or more than two of hydrochloric acid, sulfuric acid, phosphoric acid, formic acid, acetic acid and p-toluenesulfonic acid. The generation of byproducts is significantly inhibited through the addition of the stabilizer, thereby improving the yield of a target product.

Preferably, in step A, the stabilizer is p-toluenesulfonic acid.

Preferably, in step D, the mixed solution is heated to 135-138° C.

Preferably, in step D, the catalyst 1 is a mixture of one or more than two of triphenylphosphine, triethylamine and tetramethylammonium chloride.

Preferably, in step D, the catalyst 1 is a composite catalyst formed by mixing triphenylphosphine with tetramethylammonium chloride.

Preferably, in step E, the catalyst 2 is a mixture of one or more than two of methylamine, dimethylamine, trimethylamine, triethylamine, lithium carbonate and potassium carbonate.

Preferably, in step F, the catalyst 2 is lithium carbonate.

The present disclosure has the beneficial effects:

1. The present disclosure greatly simplifies the technological synthesis process of near-infrared region II fluorescent small molecules, shortens the preparation time of products, and improves the yield of products.

2. Through molecular construction, the chemical structure of the formed near-infrared region II fluorescent small molecule is stable; in the near-infrared region II fluorescent small molecule structure, the electron donor uses the bromine group, which is prone to further modifying the probe; the dioxythiophene heterocycle is prone to stabilizing the structure of the small molecule.

3. The fluorescence probe formed by the present disclosure has high fluorescence quantum yield.

4. The fluorescent probe of the present disclosure is safe for a human body.

5. The addition of the stabilizer in step A of the present disclosure inhibits the generation of byproducts and improves the yield of the target product.

6. The composite catalyst used in step D of the present disclosure improves the product yield and greatly saves energy consumption and raw material consumption while greatly reducing the reaction temperature and shortening the reaction time, 7. Such the near-infrared region II fluorescent small molecule prepared by utilizing the full organic synthesis method has the advantages of simple synthesis steps, easy modification, stable chemical structure, high fluorescence quantum yield and the like, and has huge development potential in the fields of tumor surgery navigation imaging and medical cell labeling.

DESCRIPTION OF THE EMBODIMENTS

To better understand the technical solution of the present disclosure, the present disclosure will be further described in detail in combination with drawings and specific embodiments.

Example 1

Figure 1:
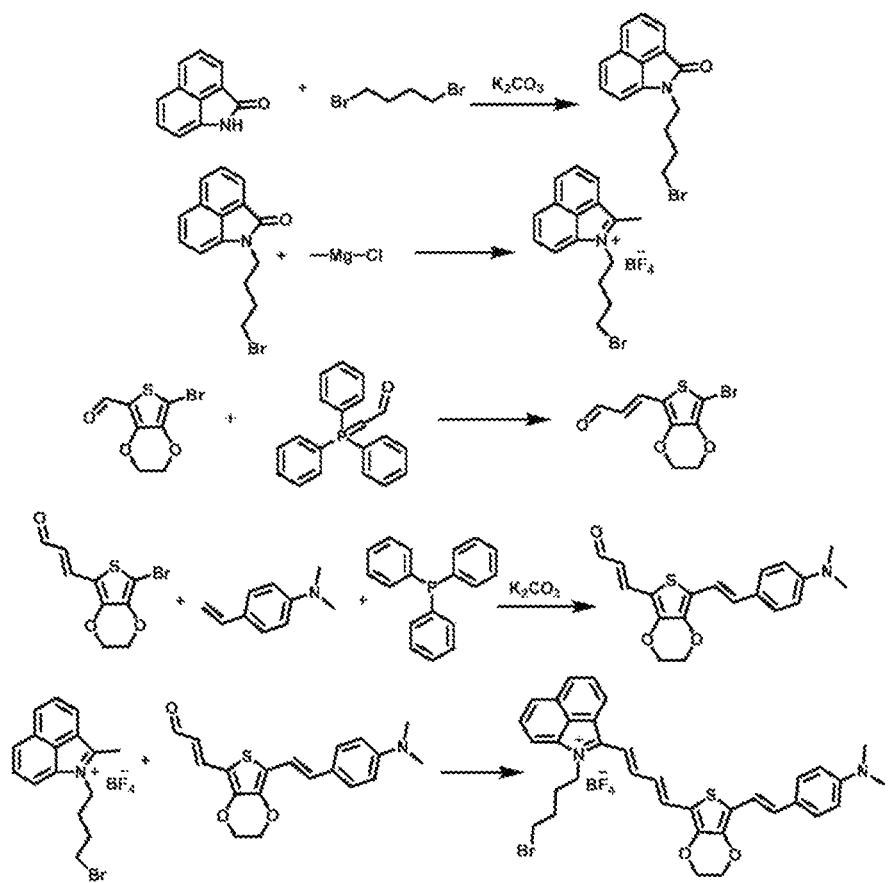
FIG. 1 is a synthesis flowchart of a near-infrared region II fluorescent small molecule.

A method for preparing a near-infrared region II fluorescent small molecule, as shown in FIG. 1, comprises the following steps:

A, synthesis of intermediate I M1

200 g of N,N-dimethylformamide, 10 g (59.1 mmol) of Benz[cd]indol-2(1H)-one and 0.14 g of anhydrous lithium hydroxide were successively added into a reactor with a stirrer and heated to 125° C. under the condition of stirring, air in the reaction system was replaced with nitrogen, 20 g (92.5 mmol) of 1,4-dibromobutane was dropwise added under the protection of nitrogen, the reaction was preserved for 30-100 min, subsequently, 1.2 g of stabilizer p-toluenesulfonic acid was added, the above materials were further stirred for 15-60 min and then subjected to reduced rectification, ethanol was added in a separated bottom liquid, and finally 16.2 g (98.505) of intermediate I M1 product was obtained by crystallizing, filtering and drying, with a yield of 92.07%;

B, synthesis of naphthalimide salt F1 the intermediate I M1 (12 g, 40 mmol) was added into anhydrous tetrahydrofuran and heated to 52° C. under the conditions of stirring and nitrogen protection, a methyl magnesium chloride solution was dropwise added, the above mixed solution was heated to 62° C. after dropwise addition was completed, the reaction was preserved for 2 h, a solvent was recycled by distillation, 50 g of water was added into the bottom liquid, 17.6 g of 20 wt % fluoroboric acid solution was slowly dropwise added at room temperature, a reaction speed was controlled, stirring was maintained for 0.5-1 h after dropwise addition was completed, and finally 10.6 g (98.2%) of naphthalimide salt F1 was obtained by suction filtration, with a yield of 90%;

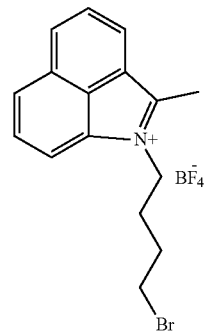

F1

C, synthesis of dioxythiophene F2

10 g (40.1 mmol) of 5-bromo-2-(3,4-vinyldioxythiophene) formaldehyde and 10 g (52.3 mmol) of (formylmethylene) triphenylphosphine were mixed in a solution of anhydrous toluene and heated to reflux, the reaction was maintained for 12 h, a solvent was evaporated at reduced pressure to obtain a crude product and the crude product was purified on a silica gel column, and finally 8.8 g (95%) of white powdered dioxythiophene F2 product was obtained by using a petroleum ether/dichloromethane (2:1, v/v) mixture as an eluting agent, with a yield of 80%;

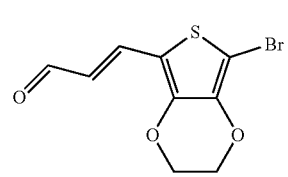

F2

D, synthesis of intermediate II M2

18.5 g of catalyst triphenylphosphine and 0.5 g of tetramethyl ammonium chloride were added into 200 g of N,N-dimethylformamide, 4-vinyl-N,N-dimethylaniline F3 (5 g, 34 mmol) and dioxythiophene F2 (6.5 g, 24 mmol) were successively added under the condition of stirring, then the mixed solution was heated to 125° C. and stirred to react for 20 h under the protection of nitrogen, the reaction solution was extracted with water and dichloromethane after the reaction was ended, each phase was separated, a combined organic phase was dried with $Na_2SO_4$ and the solvent was evaporated at reduced pressure, and finally the bottom liquid was purified by column chromatography to obtain 3.8 g (94.3%) of intermediate II M2 product, with a yield of 40.8%; and

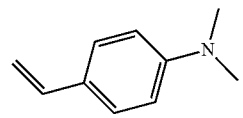

F3

E, synthesis of near-infrared region II small molecule F4

3.8 g of intermediate II M2 product and 2 g of naphthalimide salt F1 product were mixed in 30 ml of ethanol, 50 mg of lithium carbonate catalyst was added, the above materials were stirred for 6 h under the protection of nitrogen, a solvent was evaporated at reduced pressure after the reaction was ended, and then the left residue was purified by column chromatography to obtain 3 g (97%) of final product near-infrared region II small molecule F4 product by using a mixed solution of dichloromethane/methanol (2:1, v/v) as an eluting agent, with a yield of 80%.

F4

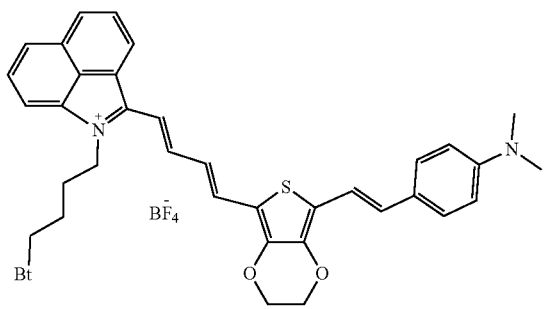

Figure 2:
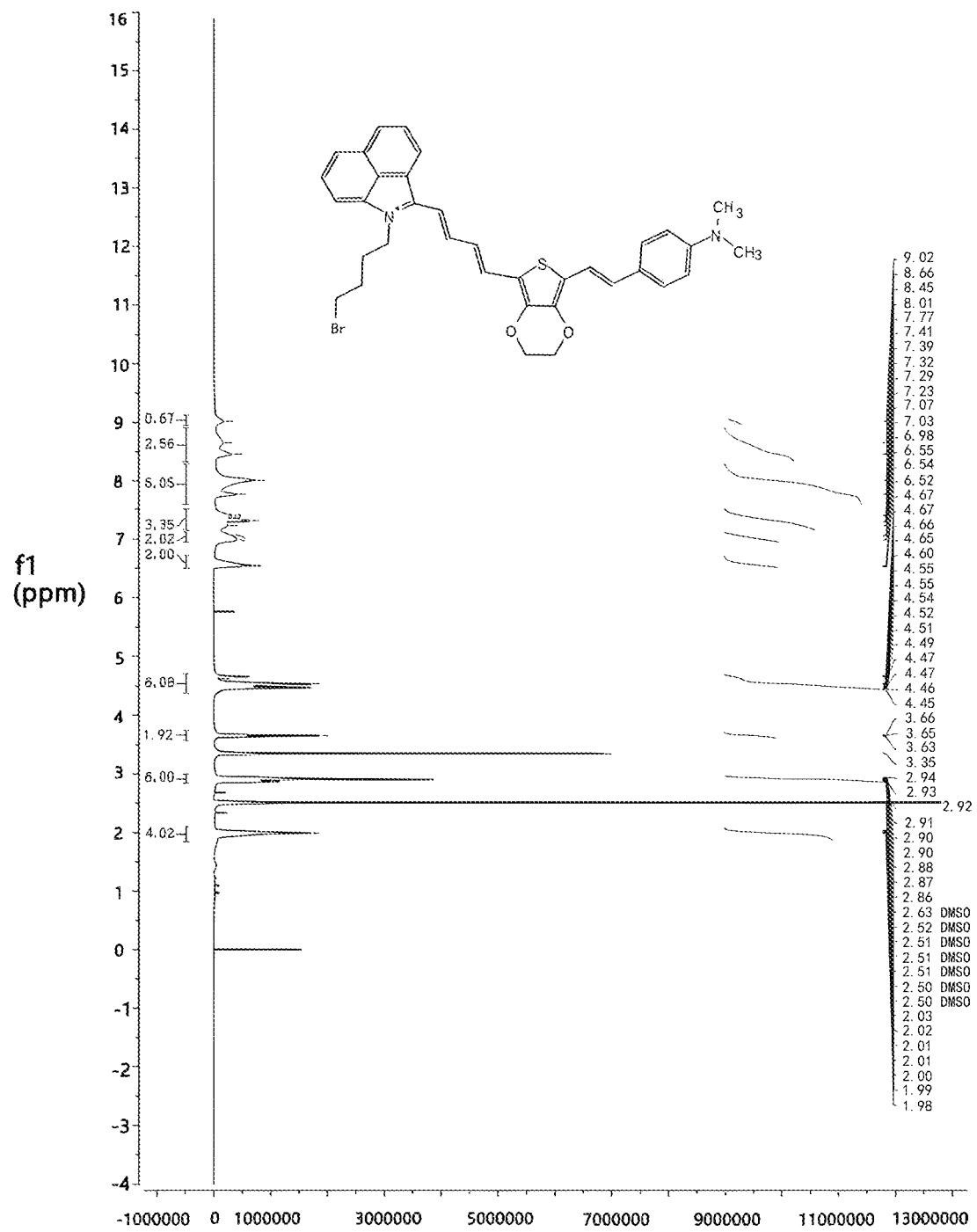
FIG. 2 is a nuclear magnetic resonance (NMR) hydrogen spectrum characterization diagram of a near-infrared region II fluorescent small molecule.
Figure 3:
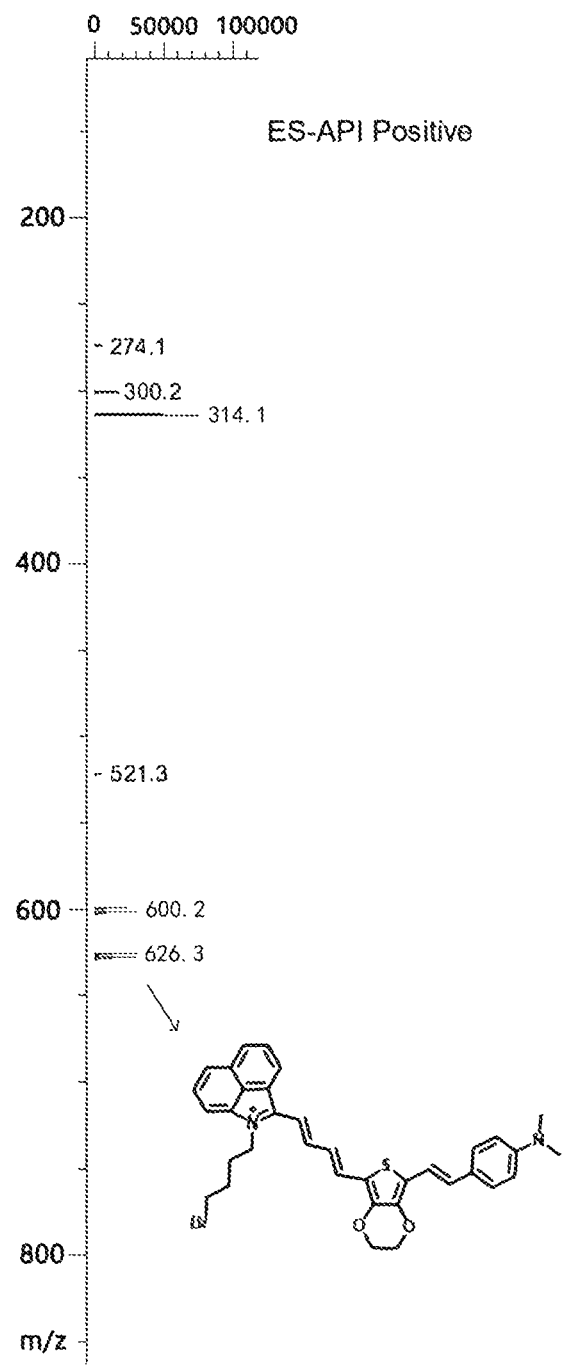
FIG. 3 is a mass spectrum characterization diagram of a near-infrared region II fluorescent small molecule.
Figure 4:
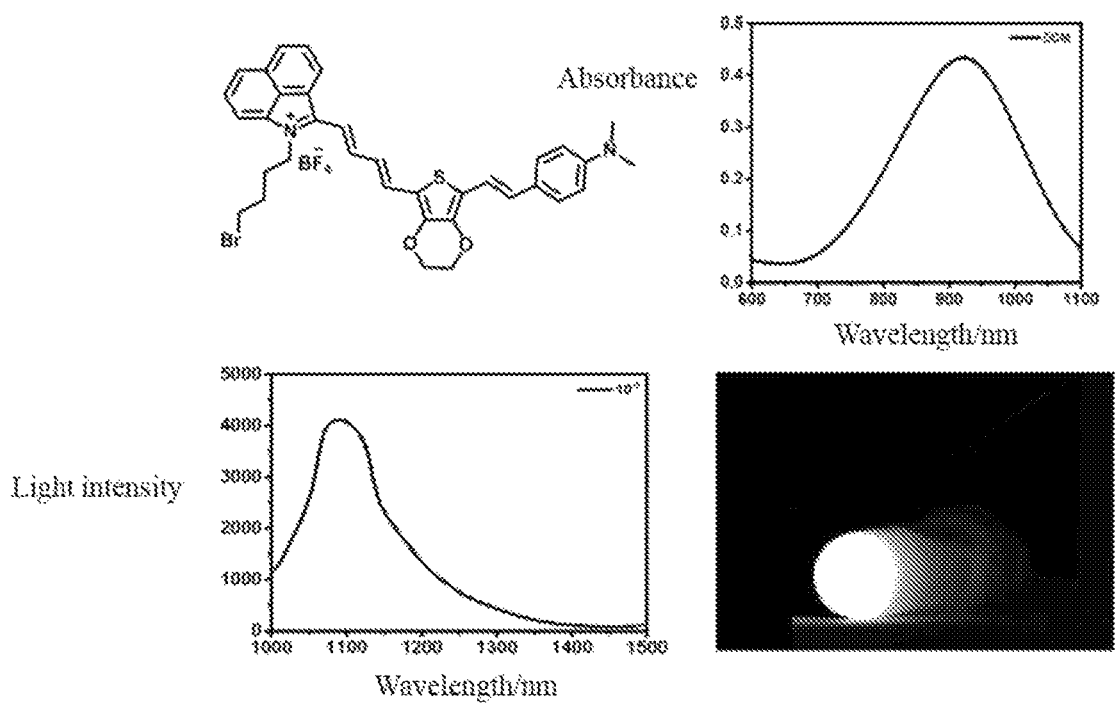
FIG. 4 is a fluorescence performance diagram of a near-infrared region II fluorescent small molecule.

As shown in FIG. 2, it is an NMR hydrogen spectrum characterization diagram of a near-infrared region II fluorescent small molecule obtained in this example. As shown in FIG. 3, it is a mass spectrum characterization diagram of a near-infrared region II fluorescent small molecule obtained in this example. As shown in FIG. 4, it is a performance diagram of a near-infrared region II fluorescent small molecule obtained in this example. When a wavelength is 900 nm, the absorbance is 0.45, which reaches a maximum value; and when a wavelength is 1100 nm, the light intensity is 4000, which reaches a maximum value.

Example 2

A method for preparing a near-infrared region II fluorescent small molecule comprises the following steps:
A, synthesis of intermediate I M1
200 g of N,N-dimethylformamide, 10.2 g (59.1 mmol) of Benz[cd]indol-2(1H)-one and 0.14 g of anhydrous lithium hydroxide were successively added into a reactor with a stirrer and heated to 150° C. under the condition of stirring, air in the reaction system was replaced with nitrogen, 20.2 g (92.5 mmol) of 1,4-dibromobutane was dropwise added under the protection of nitrogen, the reaction was preserved for 30-100 min, subsequently, 1.2 g of stabilizer p-toluenesulfonic acid was added, the above materials were further stirred for 15-60 min and then subjected to reduced rectification, ethanol was added in a separated bottom liquid, and finally 16.08 (98.32%) g of intermediate I M1 product was obtained by crystallizing, filtering and drying, with a yield of 91.32%.
The rest steps were implemented based on example 1.

Example 3

A method for preparing a near-infrared region II fluorescent small molecule comprises the following steps:
A, synthesis of intermediate I M1
200 g of N,N-dimethylformamide, 10.2 g (59.1 mmol) of Benz[cd]indol-2(1H)-one and 0.14 g of anhydrous lithium hydroxide were successively added into a reactor with a stirrer and heated to 138° C. under the condition of stirring, air in the reaction system was replaced with nitrogen, 20.2 g (92.5 mmol) of 1,4-dibromobutane was dropwise added under the protection of nitrogen, the reaction was preserved for 30-100 min, subsequently, 1.2 g of stabilizer p-toluenesulfonic acid was added, the above materials were further stirred for 15-60 min and then subjected to reduced rectification, ethanol was added in a separated bottom liquid, and finally 16.35 (98.39%) g of intermediate I M1 product was obtained by crystallizing, filtering and drying, with a yield of 92.71%.
The rest steps were implemented based on example 1.

Example 4

A method for preparing a near-infrared region II fluorescent small molecule comprises the following steps:
A, synthesis of intermediate I M1
200 g of N,N-dimethylformamide, 10.2 g (59.1 mmol) of Benz[cd]indol-2(1H)-one and 0.14 g of anhydrous lithium hydroxide were successively added into a reactor with a stirrer and heated to 138° C. under the condition of stirring, air in the reaction system was replaced with nitrogen, 20.2 g (92.5 mmol) of 1,4-dibromobutane was dropwise added under the protection of nitrogen, the reaction was preserved for 30-100 min, subsequently, 0.42 g of stabilizer formic acid was added, the above materials were further stirred for 15-60 min and then subjected to reduced rectification, ethanol was added in a separated bottom liquid, and finally 15.7 (98.18%) g of intermediate I M1 product was obtained by crystallizing, filtering and drying, with a yield of 89.01%.
The rest steps were implemented based on example 1.

Example 5

A method for preparing a near-infrared region II fluorescent small molecule comprises the following steps:
A, synthesis of intermediate I M1
200 g of N,N-dimethylformamide, 10.2 g (59.1 mmol) of Benz[cd]indol-2(1H)-one and 0.14 g of anhydrous lithium hydroxide were successively added into a reactor with a stirrer and heated to 138° C. under the condition of stirring, air in the reaction system was replaced with nitrogen, 20.2 g (92.5 mmol) of 1,4-dibromobutane was dropwise added, the reaction was preserved for 30-100 min, subsequently, 0.25 g of stabilizer hydrochloric acid was added, the above materials were further stirred for 15-60 min and then subjected to reduced rectification, ethanol was added in a separated bottom liquid, and finally 15.3 (98.23%) g of intermediate I M1 product was obtained by crystallizing, filtering and drying, with a yield of 86.74%.
The rest steps were implemented based on example 1.

Example 6

A method for preparing a near-infrared region II fluorescent small molecule comprises the following steps:
A, synthesis of intermediate I M1
200 g of N,N-dimethylformamide, 10.2 g (59.1 mmol) of Benz[cd]indol-2(1H)-one and 0.14 g of anhydrous lithium hydroxide were successively added into a reactor with a stirrer and heated to 138° C. under the condition of stirring, air in the reaction system was replaced with nitrogen, 20.2 g (92.5 mmol) of 1,4-dibromobutane was dropwise added, the reaction was preserved for 30-100 min, subsequently, 0.25 g of stabilizer hydrochloric acid was added, the above materials were further stirred for 15-60 min and then subjected to reduced rectification, ethanol was added in a separated bottom liquid, and finally 15.3 (98.23%) g of intermediate I M1 product was obtained by crystallizing, filtering and drying, with a yield of 86.74%.
The rest steps were implemented based on example 1.

Example 7

Based on example 3, in the present disclosure:
D, synthesis of intermediate II M2
18.5 g of catalyst triphenylphosphine and 0.5 g of tetramethyl ammonium chloride were added into 200 g of N,N-dimethylformamide, 4-vinyl-N,N-dimethylaniline F3 (5 g, 34 mmol) and dioxythiophene F2 (6.5 g, 24 mmol) were successively added under the condition of stirring, then the mixed solution was heated to 135° C. and stirred to react for 15 h under the conditions of stirring and nitrogen protection, the reaction solution was extracted with water and dichloromethane after the reaction was ended, each phase was separated, a combined organic phase was dried with $Na_2SO_4$ and the solvent was evaporated at reduced pressure, and finally the bottom liquid was purified by column chromatography to obtain 3.87 g (94.7%) of intermediate II M2 product, with a yield of 41.6%.

Example 8

Based on example 3, in the present disclosure:
D, synthesis of intermediate II M2
18.5 g of catalyst 1 triphenylphosphine and 0.5 g of tetramethyl ammonium chloride were added into 200 g of N,N-dimethylformamide, 4-vinyl-N,N-dimethylaniline F3 (5 g, 34 mmol) and dioxythiophene F2 (6.5 g, 24 mmol) were successively added under the condition of stirring, then the mixed solution was heated to 150° C. and stirred to react for 12 h under the conditions of stirring and nitrogen protection, the reaction solution was extracted with water and dichloromethane after the reaction was ended, each phase was separated, a combined organic phase was dried with $Na_2SO_4$ and the solvent was evaporated at reduced pressure, and finally the bottom liquid was purified by column chromatography to obtain 3.72 g (94.6%) of intermediate II M2 product, with a yield of 40.0%.

Example 9

Based on example 3, in the present disclosure:
D, synthesis of intermediate II M2
18.5 g of catalyst 1 triphenylphosphine and 0.45 g of triethylamine were added into 200 g of N,N-dimethylformamide, 4-vinyl-N,N-dimethylaniline F3 (5 g, 34 mmol) and dioxythiophene F2 (6.5 g, 24 mmol) were successively added under the condition of stirring, then the mixed solution was heated to 135° C. and stirred to react for 15 h under the conditions of stirring and nitrogen protection, the reaction solution was extracted with water and dichloromethane after the reaction was ended, each phase was separated, a combined organic phase was dried with $Na_2SO_4$ and the solvent was evaporated at reduced pressure, and finally the bottom liquid was purified by column chromatography to obtain 3.5 g (94.6%) of intermediate II M2 product, with a yield of 37.6%.

Example 10

Based on example 3, in the present disclosure:
D, synthesis of intermediate II M2
19.0 g of catalyst triphenylphosphine was added into 200 g of N,N-dimethylformamide, 4-vinyl-N,N-dimethylaniline F3 (5 g, 34 mmol) and dioxythiophene F2 (6.5 g, 24 mmol) were successively added under the condition of stirring, then the mixed solution was heated to 135° C. and stirred to react for 15 h under the conditions of stirring and nitrogen protection, the reaction solution was extracted with water and dichloromethane after the reaction was ended, each phase was separated, a combined organic phase was dried with $Na_2SO_4$ and the solvent was evaporated at reduced pressure, and finally the bottom liquid was purified by column chromatography to obtain 3.45 g (94.2%) of intermediate II M2 product, with a yield of 37.02%.

Example 11

Based on example 3, in the present disclosure:
D, synthesis of intermediate II M2
1.7 g of catalyst tetramethyl ammonium chloride was added into 200 g of N,N-dimethylformamide, 4-vinyl-N,N-dimethylaniline F3 (5 g, 34 mmol) and F2 (6.5 g, 24 mmol) were successively added under the condition of stirring, then the mixed solution was heated to 135° C. and stirred to react for 15 h under the conditions of stirring and nitrogen protection, the reaction solution was extracted with water and dichloromethane after the reaction was ended, each phase was separated, a combined organic phase was dried with $Na_2SO_4$ and the solvent was evaporated at reduced pressure, and finally the bottom liquid was purified by column chromatography to obtain 3.45 g (94.2%) of intermediate II M2 product, with a yield of 37.02%.

Example 12

Based on example 3, in the present disclosure:
E, synthesis of near-infrared region II small molecule F4
3.8 g of intermediate II M2 product and 2 g of naphthalimide salt F1 product were mixed in 30 ml of ethanol, 87.5 mg of lithium carbonate catalyst was added, the above materials were stirred for 10 h under the protection of nitrogen, a solvent was evaporated at reduced pressure after the reaction was ended, and then the left residue was purified by column chromatography to obtain 2.7 g (97.3%) of final product near-infrared region II small molecule F4 product by using a mixed solution of dichloromethane/methanol (2:1, v/v) as an eluting agent, with a yield of 72%.

Example 13

Based on example 3, in the present disclosure:
E, synthesis of near-infrared region II small molecule F4
3.8 g of intermediate II M2 product and 2 g of naphthalimide salt F1 product were mixed in 30 ml of ethanol, 64.5 mg of triethylamine catalyst was added, the above materials were stirred for 10 h under the protection of nitrogen, a solvent was evaporated at reduced pressure after the reaction was ended, and then the left residue was purified by column chromatography to obtain 2.48 g (97.03%) of final product near-infrared region II small molecule F4 product by using a mixed solution of dichloromethane/methanol (2:1, v/v) as an eluting agent, with a yield of 65.9%.

Compared with the currently studied fluorescent probe with a benzobisthiadiazole structure, the near-infrared region II fluorescent small molecule of the present disclosure has the advantages of simple synthesis method, easy modification, stable structure, high fluorescence quantum yield and the like, and is expected to be further modified to develop a novel near-infrared region II probe with more excellent water solubility and optical property, thereby providing a new probe family for study on near-infrared region II probes in the fields of tumor surgery navigation imaging and medicinal cell labeling.

The above descriptions are preferred embodiments of the present utility model. It should be noted that several improvements and modifications can also be made by persons of ordinary skill in the art without departing from the principle of the present utility model, and these improvements and modifications should be deemed as the protective scope of the present utility model.

What is claimed is:

1. A method for preparing a near-infrared region II fluorescent small molecule, wherein a near-infrared region II fluorescent small molecule with a D-π-A system structure is constructed by using a compound as a strong electron acceptor, dioxythiophene as a π bridge and an N, N-dimethylstyrene structure as an electron donor, and the structure of the compound F1 is as follows:

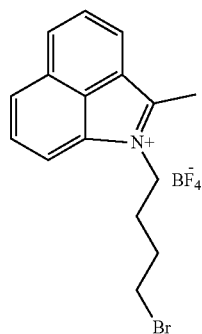

F1 the structure of the dioxythiophene F2 is as follows:

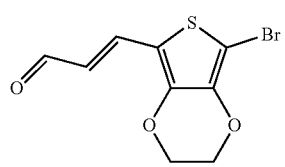

F2 the structure of the N, N-dimethylstyrene F3 is as follows:

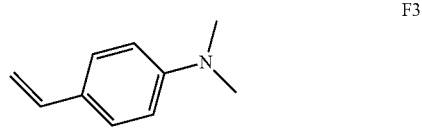

F3 the structure of the near-infrared region II fluorescent small molecule F4 is as follows:

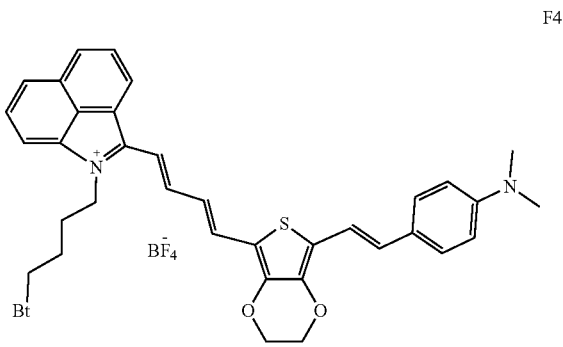

F4 the method for preparing the near-infrared region II fluorescent small molecule comprises the following steps:

A, synthesis of intermediate I M1
N,N-dimethylformamide, Benz[cd]indol-2(1H)-one and anhydrous lithium hydroxide are successively added into a reactor with a stirrer and then heated to 125-150° C. under the condition of stirring, air in the reaction system is replaced with nitrogen, 1,4-dibromobutane is dropwise added under the protection of nitrogen, the reaction is preserved for 30-100 min, subsequently, a stabilizer is added, the above materials are stirred for 15-60 min and then subjected to reduced rectification, ethanol is added in a bottom liquid, and finally the intermediate I M1 is obtained by crystallizing, filtering and drying;

B, synthesis of the compound F1
the intermediate I M1 is added into tetrahydrofuran and heated to 52-58° C. under the conditions of stirring and nitrogen protection, a methyl magnesium chloride solution is dropwise added, the above reaction is heated to 62-66° C. after dropwise addition is completed and then the reaction is preserved for 0.5-2.5 h, a solvent is recovered by distillation, a proper amount of water is added into the bottom liquid, a 20 wt % of fluoroboric acid solution is slowly dropwise added at room temperature, a reaction speed is controlled, stirring is maintained for 0.5-1 h after dropwise addition is completed, and the compound F1 is obtained by suction filtration;

C, synthesis of dioxythiophene F2
5-bromo-2-(3,4-vinyldioxythiophene) formaldehyde and (formylmethylene) triphenylphosphine are mixed in a solution of toluene and heated to reflux, the reaction is maintained for 12-18 h, a solvent is evaporated at reduced pressure to obtain a crude product and the crude product is purified on a silica gel column, and white powdered dioxythiophene F2 is obtained by using a petroleum ether/dichloromethane mixture as an eluting agent;

D, synthesis of intermediate II M2 a metered catalyst 1 is added into N,N-dimethylformamide, 4-vinyl-N,N-dimethylaniline F3 and dioxythiophene F2 are successively added under the condition of stirring, then the mixed solution is heated to 125-150° C. and stirred to react for 12-20 h under the protection of nitrogen, the reaction solution is extracted with water and dichloromethane after the reaction is ended, each phase is separated, a combined organic phase is dried with $Na_2SO_4$, the solvent is evaporated at reduced pressure, and the left residue is purified by column chromatography to obtain the intermediate II M2; and E, synthesis of near-infrared region II small molecule F4 the intermediate II M2 and the compound F1 are mixed in ethanol, a proper amount of catalyst 2 is added, the above materials are stirred for 4-12 h under the protection of nitrogen, a solvent is evaporated at reduced pressure after the reaction is ended, the left residue is purified by column chromatography to obtain the final product near-infrared region II small molecule F4.

2. The method for preparing a near-infrared region II fluorescent small molecule according to claim 1, wherein in step A, heating is carried out under the condition of stirring to raise the temperature to 138-140° C.

3. The method for preparing a near-infrared region II fluorescent small molecule according to claim 1 or 2, wherein in step A, the stabilizer is a mixture of one or more than two of hydrochloric acid, sulfuric acid, phosphoric acid, formic acid, acetic acid and p-toluenesulfonic acid.

4. The method for preparing a near-infrared region II fluorescent small molecule according to claim 3, wherein in step A, the stabilizer is p-toluenesulfonic acid.

5. The method for preparing a near-infrared region II fluorescent small molecule according to claim 1, wherein in step D, the mixed solution is heated to 135-138° C.

6. The method for preparing a near-infrared region II fluorescent small molecule according to claim 1, wherein in step D, the catalyst 1 is a mixture of one or more than two of triphenylphosphine, triethylamine and tetramethylammonium chloride.

7. The method for preparing a near-infrared region II fluorescent small molecule according to claim 1, wherein in step D, the catalyst 1 is a composite catalyst formed by mixing triphenylphosphine with tetramethylammonium chloride.

8. The method for preparing a near-infrared region II fluorescent small molecule according to claim 1, wherein in step E, the catalyst 2 is a mixture of one or more than two of methylamine, dimethylamine, trimethylamine, triethylamine, lithium carbonate and potassium carbonate.

9. The method for preparing a near-infrared region II fluorescent small molecule according to claim 1, wherein in step E, the catalyst 2 is lithium carbonate.

* * * * *